US008043562B2

(12) United States Patent
Tomasso et al.

(10) Patent No.: US 8,043,562 B2
(45) Date of Patent: *Oct. 25, 2011

(54) ANALYZER HAVING REMOVABLE HOLDERS OR A CENTRIFUGE

(75) Inventors: David Angelo Tomasso, Rochester, NY (US); Raymond Francis Jakubowicz, Rush, NY (US); James Vanselow Barry, Rochester, NY (US)

(73) Assignee: Ortho-Clinical Diagnostics, Inc., Rochester, NY (US)

( * ) Notice: Subject to any disclaimer, the term of this patent is extended or adjusted under 35 U.S.C. 154(b) by 1012 days.

This patent is subject to a terminal disclaimer.

(21) Appl. No.: 10/730,749

(22) Filed: Dec. 8, 2003

(65) Prior Publication Data

US 2005/0123444 A1    Jun. 9, 2005

(51) Int. Cl.
*G01N 9/30* (2006.01)
(52) U.S. Cl. .......................................... 422/72; 436/45
(58) Field of Classification Search .................. 422/72, 422/64; 436/43–45
See application file for complete search history.

(56) References Cited

U.S. PATENT DOCUMENTS

| | | |
|---|---|---|
| 3,826,622 A | 7/1974 | Natelson |
| 4,086,060 A | 4/1978 | Hermann, Jr. |
| 4,142,863 A | 3/1979 | Covington et al. |
| 4,269,803 A | 5/1981 | Jessop |
| 4,287,155 A | 9/1981 | Tersteeg et al. |
| 4,296,070 A | 10/1981 | Montalto et al. |
| 4,347,750 A | 9/1982 | Tersteeg et al. |
| 4,458,812 A | 7/1984 | Dreier et al. |
| 4,512,952 A | 4/1985 | Blanding et al. |
| 4,797,257 A | 1/1989 | Shaw |
| 4,815,978 A | 3/1989 | Mazza et al. |
| 4,933,291 A | 6/1990 | Daiss et al. |
| 4,965,049 A | 10/1990 | Lillig et al. |
| 5,059,393 A | 10/1991 | Quenin et al. |
| 5,089,418 A | 2/1992 | Shaw et al. |
| 5,102,624 A | 4/1992 | Muraishi |
| 5,204,269 A | 4/1993 | Barker et al. |
| 5,210,526 A | 5/1993 | Imperiali |
| 5,219,526 A * | 6/1993 | Long .............................. 422/64 |

(Continued)

FOREIGN PATENT DOCUMENTS

| | | |
|---|---|---|
| EP | 0513618 A2 | 11/1992 |
| EP | 747708 B1 | 12/1996 |
| EP | 0722089 B1 | 10/1998 |
| EP | 1464963 | 10/2004 |
| WO | WO 97/41445 A1 | 11/1997 |
| WO | WO 02/081088 A2 | 10/2002 |

OTHER PUBLICATIONS http://www.abaxisinc.com/_vet/vhem.html—Abaxis.com, VetScan® Chemistry System, Sep. 18, 2002, 2 pgs.

(Continued)

*Primary Examiner* — Natalia Levkovich
(74) *Attorney, Agent, or Firm* — Todd J. Burns (57) ABSTRACT

An analyzer, preferably a desktop analyzer, includes: a component transport system; a liquid dispense or aspirating station; a member removably located on the transport system. The removable holder includes: a probe tip dispenser; a fluid supply section for holding a sample; a test element recess for holding one or more test elements or test element holders, wherein the removable holder is configured to contain the test element recess such that a test element can be acted upon by the liquid dispense or aspirating station, while the test element is in the recess; and a measurement device to analyze a sample. Another aspect provides a removable centrifuge model on the transport system, which separates samples, such as whole blood before analysis.

9 Claims, 7 Drawing Sheets

U.S. PATENT DOCUMENTS

| | | | |
|---|---|---|---|
| 5,244,633 | A | 9/1993 | Jakubowicz et al. |
| 5,314,825 | A | 5/1994 | Weyrauch et al. |
| 5,326,398 | A | 7/1994 | Kelley et al. |
| 5,346,672 | A | 9/1994 | Staqpleton et al. |
| 5,428,470 | A | 6/1995 | Labriola, II |
| 5,441,895 | A | 8/1995 | Jakubowicz et al. |
| 5,480,484 | A | 1/1996 | Kelley et al. |
| 5,523,056 | A | 6/1996 | Miller |
| 5,525,298 | A | 6/1996 | Anami |
| 5,736,403 | A | 4/1998 | Riall et al. |
| 5,741,708 | A | 4/1998 | Carey et al. |
| 5,747,666 | A | 5/1998 | Wills |
| 5,753,512 | A | 5/1998 | Riall et al. |
| 5,787,015 | A | 7/1998 | Aldridge et al. |
| 5,885,533 | A | 3/1999 | Savage et al. |
| 5,965,447 | A | 10/1999 | Sekiyama et al. |
| 5,968,329 | A | 10/1999 | Anderson et al. |
| 5,980,830 | A | 11/1999 | Savage et al. |
| 5,983,734 | A | 11/1999 | Mathur et al. |
| 6,013,528 | A | 1/2000 | Jacobs et al. |
| 6,190,617 | B1 * | 2/2001 | Clark et al. ............ 422/104 |
| 2001/0019842 | A1 | 9/2001 | Kitamura et al. |
| 2002/0098116 | A1 | 7/2002 | Sugaya et al. |
| 2003/0017613 | A1 | 1/2003 | Jakubowicz et al. |
| 2004/0121484 | A1 | 6/2004 | Betancourt et al. |
| 2004/0191121 | A1 | 9/2004 | Tomasso et al. |
| 2004/0191923 | A1 | 9/2004 | Tomasso et al. |

OTHER PUBLICATIONS http://www.hemagen.com/Products/analyst.htm—Analyst® benchtop chemistry system, System Features, Sep. 18, 2002, 2 pgs.
Search—Nerac.com—Jan. 20, 2003—Question No. 1186511.004, 1. NDN 223-0119-8869-0: *Biochemical analysis system, and biochemical analysis element cartridge* US Pub. No. 20020098116A1.
Search—Nerac.com—Jan. 20, 2003—Question No. 1186511.004, 2. NDN 223-0118-3080-7: *Incubator* US Pub. No. 20020090322 A1.
Search—Nerac.com—Jan. 20, 2003—Question No. 1186511.004. 3. NDN 223-0118-3058-9 *Incubator* US Pub. No. 20020090321 A1.
Search—Nerac.com—Jan. 20, 2003—Question No. 1186511.004, 4. NDN 223-0107-54934: *Quantitative suction tip and quantitative suction apparatus* US Pub. No. 20020037239 A1.
Search—Nerac.com—Jan. 20, 2003—Question No. 1186511.004, 5. NDN 223-0106-44993: *Biochemical analysis apparatus* US Pub. No. 20020031844A1.
Search—Nerac.com—Jan. 20, 2003—Question No. 1186511.004, 6. NDN 223-0008-3503-0; *Analysis method using dry chemical analysis element* US Pub. No. 20010041387 A1.
Search—Nerac.com—Jan. 20, 2003—Question No. 1186511.004, 7. NDN 050-0062-9931-3: Chemical analysis system EPO Pub. No. 0932043.
Search—Nerac.com—Jan. 20, 2003—Question No. 1186511.004, 8. NDN 050-0062-9930-1, Chemical analysis system and blood filtering unit—EPO Pub. No. 0932042.
Search—Nerac.com—Jan. 20, 2003—Question No. 1186511.004, 9. NDN 050-0060-7344-0, Method of filtering blood—EPO Pub. No. 0893130.
Search—Nerac.com—Jan. 20, 2003—Question No. 1186511.004, 10. NDN 050-0054-2680-7, Blood filter unit—EPO Pub. No. 0785012.
Search—Nerac.com—Jan. 20, 2003—Question No. 1186511.004, 11. NDN 050-0049-5101-3, Chemical analysis film cartridge and method of and device for taking out chemical analysis film chip from the cartridge, EPO Pub. No. 0722089.
Search—Nerac.com—Jan. 20, 2003—Question No. 1186511.004, 12. NDN 050-0047-3882-2, Method and apparatus for spotting liquid samples onto dry-type chemical analysis film pieces, EPO Pub. No. 0877744.
Search—Nerac.com—Jan. 20, 2003—Question No. 1186511.004, 13. NDN 050-0044-8620-1, Chemical analysis film cartrige and method of and device for taking out chemical analysis film from the cartridge, EPO Pub. No. 0634859.
Search—Nerac.com—Jan. 20, 2003—Question No. 1186511.004, 14. NDN 050-0039-6047-0, Chemical analysis system, EPO Pub. No. 0555654.
Search—Nerac.com—Jan. 20, 2003—Question No. 1186511.004, 15. NDN 050-0028-3318-9, Film loading device, EPO Pub. No. 0415425.
Search—Nerac.com—Jan. 20, 2003—Question No. 1186511.004, 16. NDN 050-0017-5714-3, Automatic analytical method using chemical analytical slides, EPO Pub. No. 0285851.
Search—Nerac.com—Jan. 20, 2003—Question No. 1186511.004, 17. NDN 069-0341-4631-5, Chemical analysis stem, EPO Pat. No. 0555654.
Search—Nerac.com—Jan. 20, 2003—Question No. 1186511.004, 18. NDN 069-0338-2933-2, Method and apparatus for spotting liquid samples onto dry-type chemical analysis film pieces, EPO Pat. No. 0677744.
Search—Nerac.com—Jan. 20, 2003—Question No. 1186511.004, 19. NDN 069-327-5321-6. Method of and device for taking out chemical analysis film test elements from a cartridge, EPO Pat. No. 0722089.
Search—Nerac.com—Jan. 20, 2003—Question No. 1186511.004, 20. NDN 069-0322-6328-6, Chemical analysis film cartridge and method of taking out chemical analysis film test elements from the cartridge, EPO Pat. No. 0634859.
Search—Nerac.com—Jan. 20, 2003—Question No. 1186511.004, 21. NDN 069-0317-3206-0, Film loading device, EPO Pat. No. 0415425.
Search—Nerac.com—Jan. 20, 2003—Question No. 1186511.004. 22. NDN 069-0303-0232-0, Automatic analytical method using chemical analytical slides, EPO Pat. No. 0285851.
Search—Nerac.com—Jan. 20, 2003—Question No. 1186511.004, 23. NDN 043-0254-5389-8, Pipette Chip Loading Implement, Citation from Patent Abstracts of Japan No. 02207047 JP.
Search—Nerac.com—Jan. 20, 2003—Question No. 1186511.004, 24. NDN 043-0254-5388-6, Incubator, Citation from Patent Abstracts of Japan No. 02207046 JP.
Search—Nerac.com—Jan. 20, 2003—Question No. 1186511.004, 25. NDN 043-0254-5387-4, Incubator, Citation from Patent Abstracts of Japan No. 02207045 JP.
Search—Nerac.com—Jan. 20, 2003—Question No. 1186511.004, 26. NDN 043-0254-5386-2, Incubator Device, Citation from Patent Abstracts of Japan No. 02207044 JP.
Search—Nerac.com—Jan. 20, 2003—Question No. 1186511.004, 27. NDN 043-0252-0179-4, Cartridge for Biochemical Analysis, Citation from Patent Abstracts of Japan No. 02181834 JP.
Search—Nerac.com—Jan. 20, 2003—Question No. 1186511.004, 28. NDN 043-0252-0178-2, Biochemical Analyzer, Citation from Patent Abstracts of Japan No. 02181833 JP.
Search—Nerac.com—Jan. 20, 2003—Question No. 1186511.004, 29. NDN 043-0252-0177-0, Cartridge for Biochemical Analysis, Citation from Patent Abstracts of Japan No. 02181832 JP.
Search—Nerac.com—Jan. 20, 2003—Question No. 1186511.004, 30, NDN 043-0243-7088-2, Method and Device for Detecting Spot of Liquid, Citation from Patent Abstracts of Japan No. 02098707 JP.
Search—Nerac.com—Jan. 20, 2003—Question No. 1186511.004, 31. NDN 043-0243-7087-0, Quantitative Suction Tip and Quantitative Suction Device, Citation from Patent Abstracts of Japan No. 02098708 JP.
Search—Nerac.com—Jan. 20, 2003—Question No. 1186511.004, 32. NDN 043-0242-8766-8, Biochemical Analyzer, Citation from Patent Abstracts of Japan No. 02090377 JP.
Search—Nerac.com—Jan. 20, 2003—Question No. 1186511.004, 33. NDN 217-0406-9896-3, Chemical analysis system and blood filtering unit—U.S. Patent No. 6,241,947.
Search—Nerac.com—Jan. 20, 2003—Question No. 1186511.004, 34. NDN 217-0391-7176-6, Blood Filter Unit, U.S. Patent No. 6,170,671.
Search—Nerac.com—Jan. 20, 2003—Question No. 1186511.004, 35. NDN 217-0364-4367-6, Method of Filtering Blood U.S. Patent No. 6,170,671.

* cited by examiner

ANALYZER HAVING REMOVABLE HOLDERS OR A CENTRIFUGE

BACKGROUND OF THE INVENTION

1. Field of the Invention

The present invention relates to a diagnostic analyzer, preferably a desk top analyzer. More particularly, the present invention relates to a diagnostic analyzer having removable holders that include a probe tip dispenser, a fluid supply section and a test element recess in the same line of travel. The invention also relates to an analyzer having a centrifuge thereon.

2. Description of the Related Art

Desktop analyzers, particularly for veterinary use and point of care (POC) human use, are known in the art. For example, the Abaxis Vetscan™ and Hemagen Analyst™ are both desktop analyzers for veterinary use. The Vitros® DT-60 is a desktop analyzer manufactured by Ortho-Clinical Diagnostics Corp. Other known analyzers include those POC analyzers described in U.S. Pat. Nos. 5,968,329, 5,747,666, 5,980,830 and 5,787,015, all of which are incorporated by reference in their entireties. U.S. Pat. No. 4,965,049 also discloses a modular analyzer system. U.S. Pat. No. 5,983,734 discloses a modular automated diagnostic system. U.S. Patent Application Publication No. 2002/0098116 ('116 publication) describes a biochemical analysis system that includes a circular sample tray and a removable sample cartridge. EP 458 138 A2 discloses a diagnostic system that includes a slide compartment having a graduated microcup and pipette tip opening. U.S. Pat. No. 4,797,257 describes analyzers and their components that use slides as test elements. U.S. Pat. Nos. 5,741,708, 5,244,633, and 5,736,403 all disclose analyzers having concentric rotors. These publications are also incorporated by reference in their entireties.

Known diagnostic systems, such as those described above, have generally adequately addressed size issues but often at the expense of functionality, test menu, and productivity, or vice versa. Most known systems perform tests serially on a single patient sample, significantly limiting walk away time for the user to perform other work tasks. These analyzers usually employ a number of dedicated subsystems within the analyzer to perform discrete functions such as sample storage and positioning, reagent storage, and waste collection among others. In some cases, multiple analyzer systems are required to perform a variety of test menus needed in the lab, for example, separate systems to perform immuno rate or electrolyte assays.

In many known systems, whole blood samples must be prepared (e.g., diluted or centrifuged) prior to testing, further limiting the user's productivity. Reagent formats can be individual test strips (e.g., such as dry-slide technology), which offer the most cost effective solution and test flexibility, or multiple test formats (e.g., such as the Abaxis Vetscan™ rotor), which limit selective assay testing, and, as a result, drive up test costs. Liquid systems may compromise analytical performance when dealing with patient sample background interference compared to analyzers that use a dry-slide format. However, there are some tests which are incompatible with dry formats and therefore must use wet or liquid formats.

With systems that require separation prior to testing, separation of the sample into its components, such as blood into serum or plasma, is usually accomplished as a pre processing step by a lab technician. Centrifugation is the more common method used. The sample, such as whole blood contained in a sample tube is placed into a high-speed centrifuge to perform the separation, which can take varying amounts of time depending on the centrifuge's speed. Known analyzers can also include microcentrifuges such as described in U.S. Pat. No. 4,933,291 which describes a device that allows whole blood sample to be aliquoted into a centrifugable pipette tip. The pipette tip is then engaged by a high-speed drive that rotates the tip along its center axis. As the tip rotates, blood cells from plasma are forced upward along the angled surface of the tip into a trap or cavity near the top of the tip. After spinning, the separated plasma is then dispensed from the bottom of the tip. Published Patent Application No. 2001/0019842 discloses a microcentrifuge for separating whole blood.

There is a need for small, portable in vitro diagnostic systems that are capable of automatically performing a wide range of analysis, preferably for both human and animal health care providers, and provide the flexibility to execute a variety of operations on patient samples with a high degree of simplicity and cost effectiveness. There are a number of factors that drive the need for improved products including:

Cost Pressures—Lower cost testing solutions that more effectively utilize system reagents and operation.

Ease of Use—Users at the POC and veterinary labs are often less skilled than most technicians working in large lab operations and often perform a wide range of lab and office functions. Systems utilized in these labs must be simple to use but offer a high degree of functionality. Systems that are easy to use with little maintenance or preparation of both sample and instrument are advantageous.

Increased Test Menu Capability—Systems are needed that can perform a wide range of tests without compromising analytical performance due to test format limitations. Current systems penalize the user due to their inflexibility to accommodate individual and panel tests without additional reagent waste associated with pre-configured test formats (e.g., the Abaxis Vetscan™ rotor or the Hemagen Analyst™ Panels+ test rotor).

Size—Lab space is often very limited and portability is often a factor allowing the analyzer to be used at the patient location.

In developing such systems that achieve the above factors, there is a need to minimize the number of moving parts to save on costs and minimize space requirements. Known analyzers having removable holders (e.g., EP 458 138 A2) that include components such as slides, probe tips and sample sources do not have the components arranged in the same line of travel which results in an additional direction of motion for each subsystem. Other known analyzers (e.g., U.S. Publication No. 2002/0098116) also do not include components arranged in the same line of travel thus resulting in an additional direction of motion for subsystems to access the components. In addition, not all of the necessary components (e.g., probe tips) are arranged on the same removable holder. For analyzers requiring separation of the sample before analysis, known analyzers have not been able to incorporate a separating device such as a centrifuge, into the analyzer in a manner that allows the analyzer to minimize space requirements and provide ease of use.

The result is expensive and space consuming transport systems that are used to move various components throughout the analyzer.

SUMMARY OF THE INVENTION

One object of the invention is to overcome the disadvantages of the known art described above. Another object of the invention is to provide a desktop analyzer that can perform an array of different analysis within a compact space. Another object of the invention is to provide a diagnostic analyzer capable of positioning all test elements or samples, arranged on a common line or radius of travel, to the analyzer subsystems arranged on the same line of travel, thus minimizing the number of degrees of motion required by the subsystems. Another object is to provide a diagnostic analyzer where different tests and test formats can be employed in the same analyzer and can be easily inserted and removed from the analyzer without interrupting other ongoing analysis. Yet another object of the invention is to provide a method of transporting a component using a removable holder that presents the components in the same line of travel. Still another object of the invention is to provide a diagnostic analyzer having subsystems, such as a centrifuge arranged on a common line or radius of travel to other analyzer subsystems. Yet another object of the invention is to provide a method of analyzing a sample.

The foregoing and further objects of the invention are accomplished according to one aspect of the invention that provides an analyzer, which includes: a transport system; a liquid dispense or aspirating station; a member removably located on the transport system. The removable holder includes: a probe tip dispenser; a fluid supply section for holding a sample; a test element recess for holding one or more test elements or test element holders, wherein the removable holder is configured to contain the test element recess such that a test element can be acted upon by the liquid dispense or aspirating station, while the test element is in the recess; and a measurement device to analyze a sample. In a preferred embodiment, the analyzer is a desktop analyzer.

Another aspect of the invention provides an analyzer which includes: a transport system; a liquid dispense or aspirating station; and a removable centrifuge module removably located on the transport system, wherein the centrifuge is adapted to receive a sample from the liquid dispense or aspirating station or provide a separated sample to the liquid dispense or aspirating station; and a measurement device to analyze a sample. Preferably, this aspect of the invention includes a centrifuge station that has a drive to engage and to provide rotary motion to the centrifuge cup of the centrifuge module.

According to another aspect of the invention there has been provided, a method of transporting a probe tip, a liquid supply system for containing a sample to be analyzed and a test element to a subsystem in an analyzer. The method includes: providing the probe tip, liquid supply system and test element; arranging the probe tip, sample reservoir and test element on an component transport system on the same line of travel of the transport system; and moving the probe tip, sample reservoir and test element past the subsystem. Yet another aspect of the invention provides a method of analyzing a sample, which includes: arranging a sample in a sample reservoir, at least one test element and a probe tip on a first rotor on the same line of travel of a transport system; and moving the transport system to align the probe tip with the proboscis of a liquid dispense and aspirating station; engaging the probe tip with the proboscis; moving the transport system to align the sample reservoir with the liquid dispense and aspirating station; aspirating sample from the sample reservoir; moving the transport system to align the test element with the liquid dispense and aspirating station; and dispensing the sample onto the test element, wherein the liquid dispense and aspirating station has substantially no lateral movement.

Yet another aspect of the invention provides a method of analyzing a sample, which includes: arranging a sample in a sample reservoir, at least one test element and a probe tip on a first rotor on the same line of travel of the first rotor; rotating the first rotor to align the probe tip with the proboscis of a liquid dispense and aspirating station; engaging the probe tip with the proboscis; rotating the first rotor to align the sample reservoir with the liquid dispense and aspirating station; aspirating sample from the sample reservoir; rotating the first rotor to align the test element with the liquid dispense and aspirating station; dispensing the sample onto the test element, wherein the liquid dispense and aspirating station has substantially no lateral movement; rotating the first rotor to align the test element with a test element transfer station; transferring the test element to a second rotor; incubating the test element; rotating the second rotor to bring the test element into cooperation with a measurement device; and measuring the sample with the measurement device. Preferably, the methods described above are implemented by a computer program interfacing with a computer. The present invention also provides an article of manufacture, which includes a computer usable medium having computer readable program code configured to conduct the methods described above.

Further objects, features and advantages of the present invention will be apparent to those skilled in the art from detailed consideration of the preferred embodiments that follow.

DETAILED DESCRIPTION OF PREFERRED EMBODIMENTS

The present invention is directed to an in vitro analyzer for use in human and animal diagnostics, preferably a desk-top analyzer. The analyzer of the present invention allows for simplified panel testing, e.g., a "chem 7" or "chem 20" panel, with the option to add individual tests as required by the user without generating unnecessary reagent waste or unwanted tests. The device is simple to use and allows the user the opportunity to place multiple patient samples on the device that will automatically process the tests without further intervention by the user.

As used herein, "component," singular or plural, is defined as any object used to manipulate, contain, or modify the sample, consumable or otherwise. "Component" can include test elements (defined below), probe tips, probe tip holders or dispensers, and fluid supply section (including sample and other fluid reservoirs). Component also includes sample and all reagents, including washes and diluents.

In order to make such a compact design possible, one aspect of the present invention provides a diagnostic analyzer that includes holders removably placed on the transport system (also referred to as a conveyor system) that include the components arranged on the holder in the same line of travel to intersect the subsystems (e.g., liquid dispense or aspirating station) when the holder is transported past the subsystem. This reduces the degrees of motion that the subsystem has to articulate or traverse, which in turn, reduces the need for complex transport and control systems, required for the subsystem(s). With the removable holders of the present invention, the stationary probe described in the copending application entitled "Analyzer Having a Stationary Multifunction Probe" filed on Mar. 31, 2003 as Ser. No. 10/403,266 and incorporated by reference in its entirety, is advantageously used.

Along those same lines in order to minimize size, other subsystems, such as a centrifuge module or waste collection container can also be removably placed on the transport system in order to intersect the subsystems (e.g., liquid dispense or aspirating station or centrifuge station) when the other subsystems are transported past the subsystem.

As noted above, a holder that is removably attached to a transport or conveyor system is provided in conjunction with the analyzer. Three components including a probe tip dispenser, a fluid supply section (e.g., a sample reservoir) and test element recess (shown as reference no. 53 if FIG. 2) are included as part of the holder. The components are aligned on the holder such that they will be in the same line of travel (or the same centerline) as each other. That is, each component will intersect the same x, y coordinates as the other components (see FIG. 4). There may be some variability depending on the height of the component in the vertical "z" direction. In a preferred embodiment when the component conveyor is a rotor, the removable holder is in the shape of a sector (as viewed from the top) that sits on the rotor. Two of the sidewalls are arcuate in shape (with the inner sidewall facing the center of the rotor being shorter) and the other two sidewalls (or endwalls) are straight. Of course, if the transport system is linear, the removable holder may be in the shape of a rectangle.

The removable holder is preferably of a one-piece construction. One component in the removable holder is a probe tip holder or dispenser which retains a tip that will be used to aspirate the fluid in the fluid supply section. Another part of the removable holder is a fluid supply section contains the fluid, such as whole blood, serum plasma, reagent wash fluid, or a diluent to be aspirated and dispensed onto the test element. That is, the fluid supply section can be a sample or reagent reservoir. The other component that is included in the member is the test element recess for holding the test element or test element holder described more fully below. The test element recess preferably is positioned between the probe tip holder and the fluid supply section. Thus, in one unit, all components of the analyzer that are required to be moved into registration with a subsystem, such as an aspirating or dispensing station can be included in the fluid supply section on the first rotor.

An advantage of the present invention, noted above, lies in the ability to use multiple removable holders to handle different types of assays and formats. For example, one removable holder could be used for wet-format assays and the other member could be used to hold dry slide format assays. Alternatively, one holder could be used for one type of dry-slide assays (e.g., a chem.-7 panel) and the other holder could be used for another type of dry-slide assays (e.g., selected slides for immunodiagnostic tests).

In the present invention, the transport system is preferably a concentric rotor system. The first rotor, preferably the outer rotor, is used to transport all components or other parts or subsystems such as the waste collection container or centrifuge module, into proper registration with each other to perform the operations, e.g., sample dispense onto a test element, necessary for analysis. The transport system is also able to provide the motion that would normally be performed by a subsystem, e.g., the fluid supply system, for proper registration of components with subsystems or subsystems with subsystems, etc. By using a single transport system for the majority of, if not all, operations, with the removable holders or removable subsystems of the present invention, the number of moving parts and the size of the system can be significantly reduced while maintaining full system functionality, which is important in smaller analyzers, such as desktop analyzers.

As noted above, the transport system in the present invention is preferably concentric rotors, which are known in the art as described in the publications cited above. In the present invention, the first rotor, preferably the outer rotor, is used to transport components and/or subsystems. The second rotor, preferably the inner rotor is used to incubate samples being analyzed and to align the test element containing the sample with a measurement device such as a spectrometer.

The transport system can be actuated by drive and control systems well known in the art, such as those described in U.S. Pat. No. 4,287,155 and U.S. patent application Ser. No. 09/904,692 entitled "Tandem Incubator for Clinical Analyzer" filed on Jul. 13, 2001, both of which are hereby incorporated by reference in their entireties. The first rotor transporting the components can also include features for ensuring proper registration of the components, the removable holder(s) holding the components, e.g., the movable fluid supply described below, or subsystems on the first rotor. For example, the registration features can be in the form of a peg and hole, a spring loaded latch, etc.

The second rotor, preferably the inner rotor, which is used in conjunction with an incubator, generally will only hold the test element, e.g., a slide, that has already had the sample applied or added to it. To move test elements from the first rotor into the second rotor, a subsystem such as a test element transfer station or mechanism is preferably provided. In some instances, however, it is envisioned that the test elements could be manually transferred between rotors by an operator. The transfer mechanism may also be used to eject a test element after it has been measured by the spectrometer. In one embodiment, the transfer mechanism has one or more devices known in the art as slide insert mechanisms to move slides from one point to another. They are usually a metal or plastic blade driven by a motor that pushes the slide into position. Similar transfer mechanisms are used on the VITROS® series of analyzers made by Ortho-Clinical Diagnostics, Inc., except that in the present invention a shorter version would be used due to size constraints. In addition, in a preferred embodiment, the present invention will have two slide shuttle mechanisms at a fixed position facing each other. They will be able to work independently or together to move the slide to any position on the outer or inner rotor for processing. Publications disclosing similar transfer mechanisms include U.S. Pat. Nos. 5,059,393 and 4,269,803, both of which are incorporated herein by reference in their entireties.

The dispensing or aspirating station (i.e., probe) usable in the present invention can include any suitable construction capable of manipulating a fluid in a desired manner, such as those described in U.S. Pat. No. 4,965,049. The probe is preferably a nozzle having a proboscis that holds a probe tip. The probe also preferably both aspirates and dispenses fluids. Unlike known probes used in analyzers, the concentric rotors of the present invention do not require the probe to have complicated movements. That is, one embodiment of the present invention also provides a stationary fluid probe. As used herein, "stationary" is defined as the probe being stationary along at least one axis of an x, y and z coordinate system. Preferably, the probe is only movable along a single axis, such as the vertical "z" axis. Movement in the vertical direction allows the probe to access probe tips, samples, waste, etc., which may be at different heights. Thus, with the exception of vertical movement of the probe, all movement is confined to the removable holder, which is transported by the moving rotor. In other words, the probe, via the aspirating and dispensing station, has substantially no lateral movement. Again, this is made possible, in part, by the inventive configuration of the removable holder that presents each of the components in the same location doing away with an additional motion or travel required by the subsystem. This has the significant advantage over typical known analyzers in that additional cost and complexity that would result from a probe transport system is avoided. That is, a simple control system in one dimension (in this case vertical) is all that is required for the stationary probe, as opposed to a more complex control system required for more degrees of freedom. Thus, instead of a complex transport and control systems as used in known analyzer probe transports (i.e., multiple servo motors and controllers being provided) a much simpler transport and control system is all that is required. Further details of the stationary fluid probe can be found in co pending application entitled "Analyzer Having a Stationary Multifunction Probe" described above.

Also, in some embodiments, such as that described below, an additional fluid probe, such as a reference fluid dispensing nozzle, may also be provided. Due to space limitations, it may be desirable to have some movement of the additional probe, such as to move from a fluid source, e.g., a source of reference fluid, to the dispense position over the test element. In such an instance, the movement of the additional probe could be limited to movement in a straight line or a single plane, due to the position of one opening of the probe guide, described below, which would be disposed to receive the additional probe. This would simplify construction by dispensing with the requirement of providing motion and control systems for three dimensional movement. Further details of the additional fluid fixed probe, can be found below and in co-pending application described entitled "Analyzer Having a Stationary Multifunction Probe."

A test element can be located in the test element recess of the removable holder. The test element can be a slide containing the reagents necessary for the analysis, the so-called dry-slide technology as described in U.S. Pat. No. 4,797,257 or a cup-shaped well or test reaction container as described in U.S. Pat. No. 5,441,895 (these are designated as block box 54 in FIG. 1), which are incorporated by reference in their entireties. The test element can also be the so-called test strip chemistry.

A test element holder (i.e., a genus of cartridge 23 as shown in the Figures), which can also be located in the test element recess, contains test elements to be dispensed. Typically this would include multiple test elements, however, in some embodiments, such as wells for a wet analysis, it can be envisioned that a single test element may be employed. The holder can also be termed a cassette. The holder includes a body portion for holding at least one test element and a guide adapted to receive a probe to position the probe in a desired registration with the test element. Preferably, the test element holder includes a recess for holding the test elements and a cover for the test element or other fluid source being acted upon by the probe. Suitable cassettes are described in U.S. Pat. Nos. 4,142,863 and 4,512,952, both incorporated by reference in their entireties.

Located within the cover is at least one opening, preferably two and more preferably three openings adapted to receive the probe tip. The opening(s) can include a surface that extends away from the opening and at least partially surrounds the opening(s). Preferably, the openings are round and the surface has at least a partially cylindrical shape. The surface can open in an increasing manner in a direction away from the hole toward the probe tip to assist in guiding the probe into registration with the test element. For example, the surface can have the shape of a truncated cone.

Figure 2:
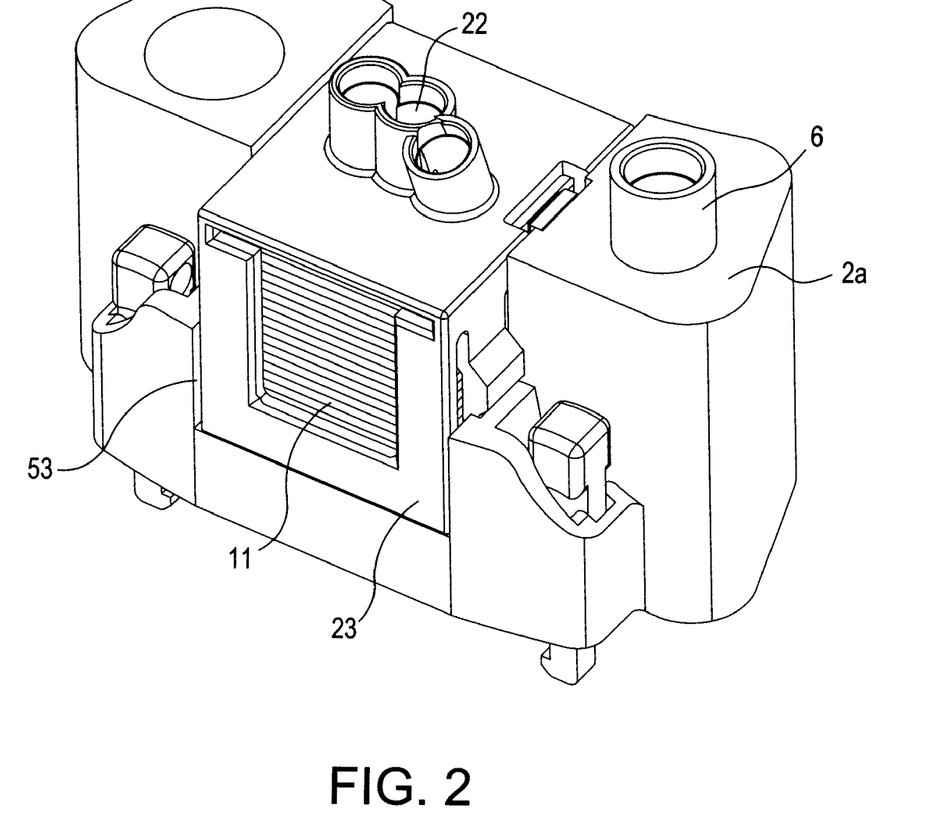
FIG. 2 shows a perspective view of a removable holder that includes a test element holder with a probe guide according to one embodiment of the present invention.

In one embodiment, there are a plurality of openings and one of the openings opens in a direction that is different than the other openings. This can be provided for a variety of reasons. For example, in some embodiments, there may be provided multiple probes, such as one for sample and the other for reference fluids for potentiometric analysis as described above, that are positioned at different angles with respect to the test element or other fluid sources. In this embodiment, the other opening can receive the probe in the same manner as the other opening that have an opening perpendicular to the covering of the test element. It should be understood that the description of the plurality of holes above encompasses designs where the holes share common sectors with each other, such that there are no discontinuities between holes. That is, the holes overlap to a certain extent. This is illustrated in FIG. 2. This allows the probe tips to be positioned closer to each other than if the probe guide holes were completely separate. Exemplary probe guides can be found in U.S. Pat. No. 4,797,257, described above.

The probe guide can be an integral or unitary one-piece construction with the test element holder, or a separate attached structure. In a preferred embodiment, the guide alone or the integral guide and test element holder are formed from an injection molded plastic. In some embodiments, the test elements may come pre-packaged in a disposable test element holder. In these embodiments, the probe guide may likewise be disposable, preferably recyclable. Of course, if the probe guide is separately attachable to the test element holder, it can be independently disposable. At least periodic disposal is particularly advantageous, because it dispenses with cleaning requirements, reduces the likelihood of carry-over between samples and reduces tolerance buildup due to wear. Further details of the test element cartridge and guide can be found in co pending application entitled "Test Element Holder with a Probe Guide for an Analyzer" filed Mar. 31, 2003 as Ser. No. 10/403,153 and incorporated by reference in its entirety.

In another preferred embodiment of the invention, a plurality of test element holders with probe guides are provided. By providing a test element holder with a corresponding probe guide, different test elements, such as potentiometric and calorimetric test elements, or wet and dry test elements, can be used together on a single analyzer, providing a significant benefit in reducing size and providing optimum flexibility in analysis. Further details of multiple test element holders are described in co pending application described above entitled "Test Element Holder with a Probe Guide for an Analyzer." The materials of construction for the analyzer, including the concentric rotors can include all suitable materials known in the art, such as plastic or metal. The disposable items of the analyzer, such as the test elements, test element holder and metering tips are preferably made from environmentally friendly, recyclable materials.

Another aspect of the invention provides an analyzer that includes a centrifuge module that is removably located on the transport system as described above. In this aspect of the invention, the centrifuge module can be used separately from the removable holder, but is preferably used together with the removable holder in order to better achieve the advantages of compactness. The centrifuge module includes a housing containing a centrifuge cup. The centrifuge cup receives the sample to be separated. In a preferred embodiment, the cup is conically shaped and has an annular cavity wrapped concentrically around the cup at the top as described in U.S. Pat. No. 4,933,291 and as shown in the preferred embodiment described more fully below. The cup is supported in the housing by bearings to allow rotation of the cup relative to the housing. To rotate the centrifuge cup, a centrifuge station is supplied on the analyzer in line with the transport system in a similar manner to the dispense and aspirate station. The centrifuge station engages the top of the centrifuge cup, and spins the cup with a motor that can include an electric or pneumatic motor capable of rotating the cup at speeds of 30,000 to 100,000 RPM as described in the '291 patent, which is incorporated herein by reference in its entirety.

Another aspect of the invention provides a method of transporting components, including the probe tip, fluid supply section and test element or subsystems, such as a centrifuge module in an analyzer, preferably a desktop analyzer, along the same line of travel past another subsystem, such as a dispense or aspirating station as described above. Preferably in this method of the invention, the components are arranged on transport system on a removable holder.

In another preferred embodiment, the first rotor is used to transport the various components, such as the test element, test element holder, sample, reagent, etc. or other parts, e.g., waste collection container or centrifuge module, into registration with each other. The second rotor is preferably only used to incubate and transport the test element to the measurement device (e.g. a spectrometer or electrometer). Another important feature is that the various subsystems, such as the fluid liquid probe have their motion restricted to save on room and expense. Instead, the first rotor, in combination with the same line of travel or centerline provided by the placement of the components on the removable holder, performs the necessary motion that the subsystems would have performed. For example, the stationary fluid probe in a preferred embodiment is only capable of motion in the vertical direction. All other motion required for bringing the fluid probe into necessary registration with the test element, etc. is provided by the first rotor.

The present invention also provides a method of analyzing a sample. In one preferred embodiment, the type of analysis or test to be performed on a sample is selected. Based on the test to be performed, one or more movable test elements, corresponding to the test to be performed, are loaded onto the analyzer, preferably in the removable holders. The test elements preferably contain identification indicia or marks, such as a barcode, that can be read by the analyzer to determine the test to be performed and the physical dimensions of the test element. In some instances the analysis to be performed is also inputted into the control system for the analyzer, preferably through a keyboard of a computer that controls the analyzer.

A sample in a sample reservoir is provided, preferably on the removable holder, along with a probe tip. The removable holder containing the sample and test elements is loaded onto the analyzer. Depending on the number and type of analysis to be performed, more than one removable holder may be required. Upon activation of the analyzer, the first rotor moves the movable fluid supply into registration with a liquid dispense and aspirating station, such as the stationary fluid probe. In some embodiments the proboscis of fluid probe first receives the disposable probe tip. The proboscis can receive the tip by lowering the proboscis into engagement with the tip or by raising the tip into engagement with the proboscis. The sample is then moved into registration with the fluid probe and the probe aspirates sample into the tip. After aspirating the sample, the test elements are moved into registration with the fluid probe by rotation of the first rotor. A pre-selected amount of the sample is dispensed from the probe tip onto or into the test element. If necessary, a supply of liquid reagent, such as horseradish peroxide oxidase ("HPO"), can be moved into registration with the stationary fluid probe. The probe aspirates the reagent and retains the reagent until the sample has moved back into registration with the probe, at which point the reagent is dispensed onto the test element containing the sample. As is clear from the description above, a significant advantage of the present invention is that by having the test element, sample reservoir and disposable probe tip lie in the same line of travel, additional movement, other than vertical ("z" axis) movement by the subsystems such as the dispense and aspirating probe is not required.

At this point, if incubation is required, the test element containing the sample, can be incubated. To accomplish this, the test element is transferred to the inner rotor by the test element transfer mechanism and incubated (such incubators are well known in the art and are depicted as black box 52 in FIG. 1), while the outer reagent rotor continues the function of transporting sample and test elements into registration with the stationary probe. After incubation, the sample can be optionally washed, once again, by moving a supply of liquid wash into registration with the stationary probe. After washing, the sample can be transferred to a spectrometer or other analyzer (such analyzers are well known in the art and are shown by the hidden black box 51 in FIG. 1) to have its signal measured. On chemiluminescent applications where a signal reagent is needed, once again, a supply of signal reagent is moved into registration with the probe to be aspirated and then dispensed onto the washed sample. After completion of the analysis, the test element can be disposed of. To accomplish this, the second ring is brought into registration with the waste collection container on the first ring and ejected into the waste collection container with the test element dispense mechanism. Likewise, the outer reagent rotor can rotate the waste container into alignment with the stationary probe and receive the used probe tip(s).

In those embodiments where a separation of the sample is required, after the initial aspiration of the sample, the rotor rotates a separation device, preferably the centrifuge module described above, into alignment with the liquid dispense and aspiration station, where the aspirated sample is dispensed into the centrifuge. The centrifuge module is then rotated to a centrifuge station where the centrifuge cup is engaged and spun to separate the sample into its constituents, e.g., blood into plasma and red blood cells. The centrifuge cup is then disengaged from the centrifuge station and the centrifuge module is rotated back to the liquid dispense and aspiration station where further analysis of the sample is continued.

The present invention will now be illustrated in connection with the following detailed preferred embodiment. Of course, the preferred embodiment is intended for illustrative purposes only and is not intended to limit the scope of the invention.

The analyzer includes the removable holders containing the components including the probe tip dispenser, test element recess and fluid supply section, all of which were described above. The analyzer also includes the concentric rotors described above. Samples may be whole blood, which may be automatically centrifuged prior to metering or more preferably centrifuged on the analyzer using the centrifuge module, or a variety of other sample types including serum, plasma and urine, among others. The concentric rotors work in concert to process a wide variety of analytical tests with little intervention by the user.

The first, e.g., outer, reagent rotor carries the removable holders and eliminates the need for multiple system modules and associated complexity since it is capable of storing and processing samples, test elements, liquid reagents, disposables and waste on a single platform. The multifunctional first, outer reagent rotor allows the user to place multiple patient samples on the rotor in addition to individual, assay specific test slides in test cartridges. The removable holder also accepts whole blood samples, which can be automatically centrifuged on the analyzer or prepared samples. The first, outer reagent rotor is also capable of positioning a variety of removable holders in various formats that allow for auto dilution of samples and expanded test menu capability through the addition of wash fluids for immuno rate assays. The reagent rotor is also capable of accepting a waste collection container to collect the various test slides and metering probe tips and other subsystems, such as the centifuge module. The outer reagent rotor is automatically positioned to intersect a fixed metering system, that includes the fluid probe, used to aspirate and dispense various fluids.

The second inner incubator rotor is used to incubate the test slides followed by positioning at a measurement device such as a spectrometer or electrometer. Test slides are then ejected from the incubator rotor into the waste collection container placed on the outer reagent rotor. The waste collection container is also able to collect other test consumables such as disposable probe tips due to the random access positioning capability of the reagent rotor.

All test processing and waste collection is accomplished within the rotors. Additional system features not shown can include an integral printer, user interface keypad/display, electronics and cabinetry all of which are known in the art.

Figure 1:
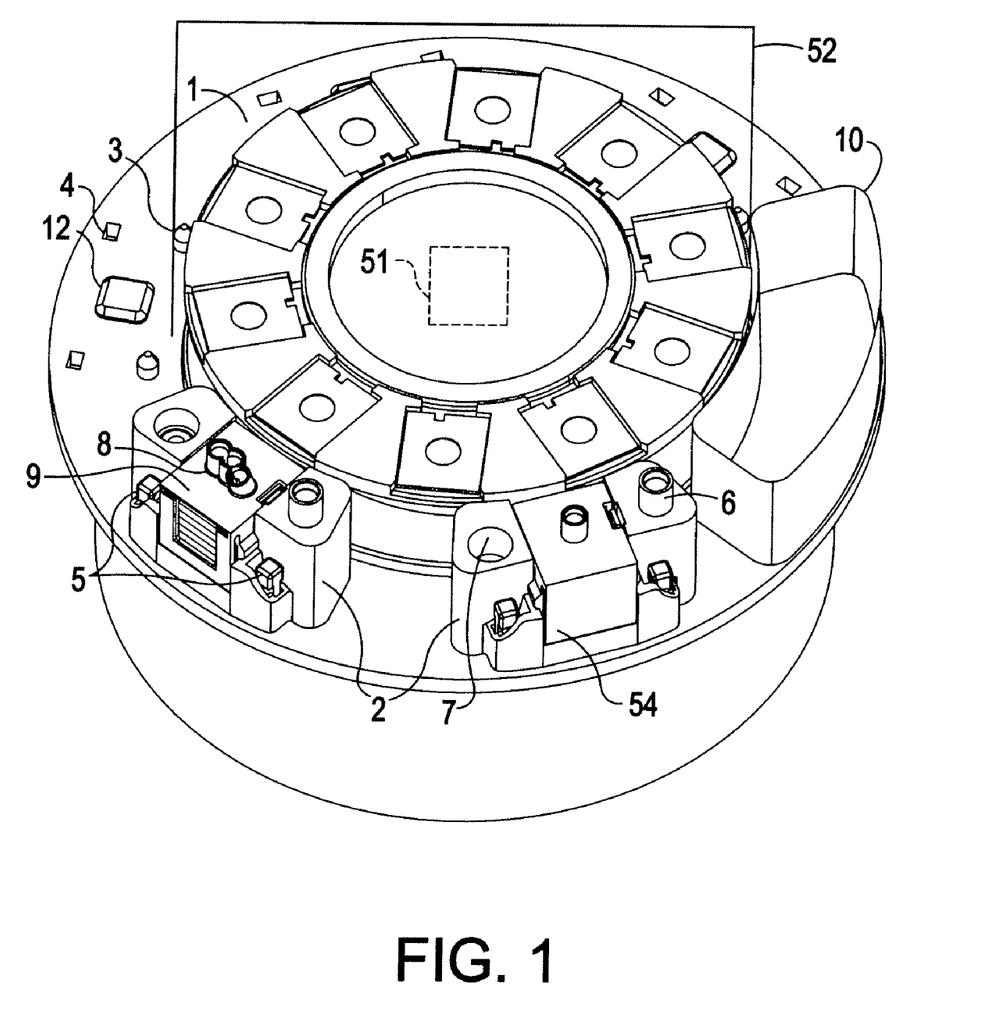
FIG. 1 shows a perspective view of a desktop analyzer according to one embodiment of the present invention.
Figure 5:
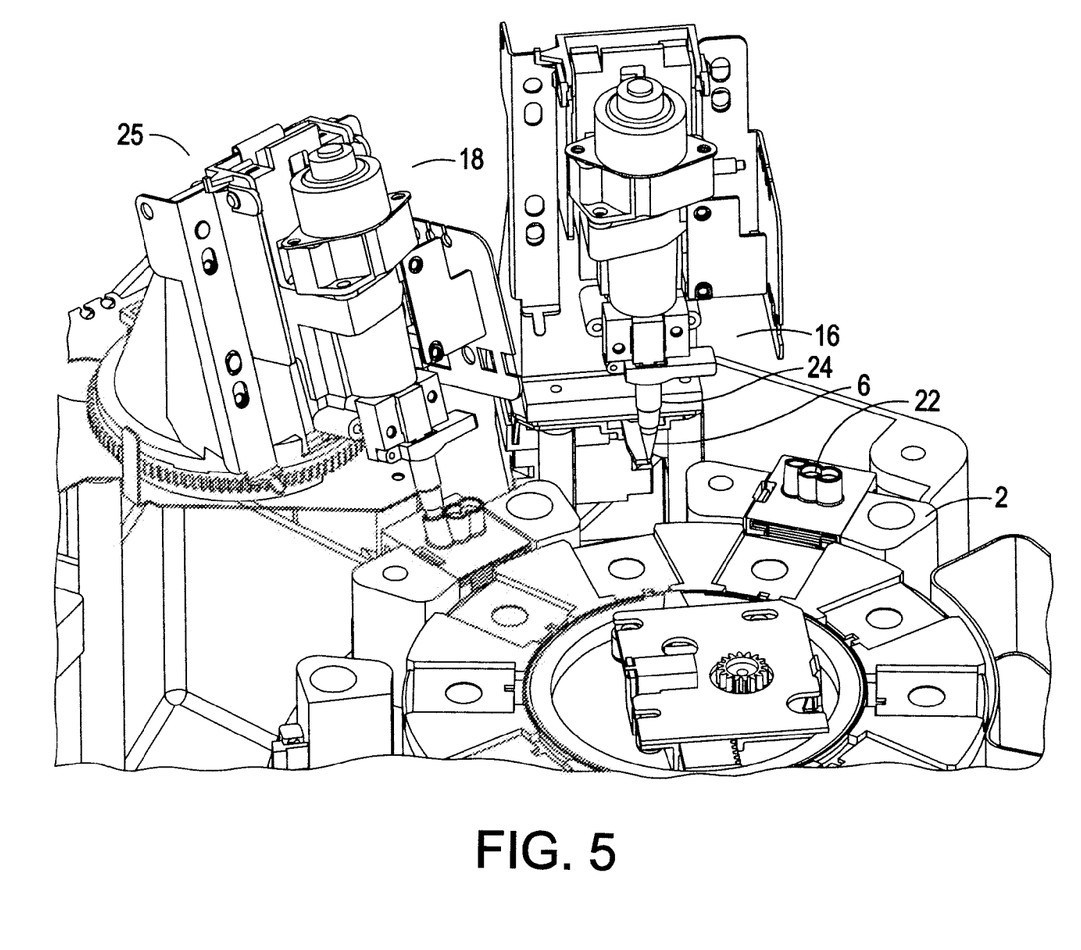
FIG. 5 shows a perspective view of an analyzer with the outer and inner concentric rotor according to one embodiment of the invention.

In the embodiment shown in FIG. 1, the first reagent rotor (1) orients removable holders (2) concentric to the rotational axis of the reagent rotor (1). The reagent rotor is rotated about its center axis by a motor with a sensor to determine exact positioning. The removable holders (2) are reusable and are accurately positioned on the reagent rotor using a locating or registration feature (3), which in this embodiment is a peg that inserts into a hole (not shown) on the underside of the removable holder (2) and anti-rotation feature (4), which in this embodiment is a recess that will accept a pin attached to the end of a spring-loaded latch (5). The removable holders (2) are held in place on the reagent rotor by spring-loaded latches (5) or other means that allow easy loading and unloading of the removable holders (2) by the user. A single disposable metering tip (6) is placed in a recess (probe tip dispenser) on the top of the removable holder (2) for access by the metering system 16 (i.e., probe). A patient's sample is placed in a corresponding recess (7) (sample reservoir) along the same centerline for access by the metering system. A probe guide (8) for metering registration is located on the top of, and in this instance integral with, the holder or cartridge (23) (in this case for test slides) to allow for accurate positioning of the metering probe tip (24, as shown in FIG. 5) during sample dispense onto the slides in the cartridge or holder. The probe guide includes cover (9) and one or more holes (22, FIG. 2). The reagent rotor will also accept a variety of different cartridges (23) that expand the functionality of the system at the discretion of the user. These may include diluent cartridges for performing sample dilutions, immuno rate wash cartridge for performing a wash step prior to final reading of immuno rate chemistries among other cartridge formats that are possible. A waste collection container (10) is also positioned on the reagent rotor and is positioned to automatically collect used metering tips and slides after testing is complete.

As shown in FIG. 2, test slides (11) are loaded into the cartridge (23, FIG. 1) prior to processing on the analyzer. The cartridge is capable of accepting a predetermined panel of test slides as well as individual test slides. The test slides (11) are registered up against the inside top surface of the test cartridge directly under the metering registration features by a spring-loaded plunger (12, FIG. 1) mounted to the reagent rotor. The cartridge is loaded into the removable holder (2), which is shown in FIG. 2 off the analyzer conveyor.

Figure 3:
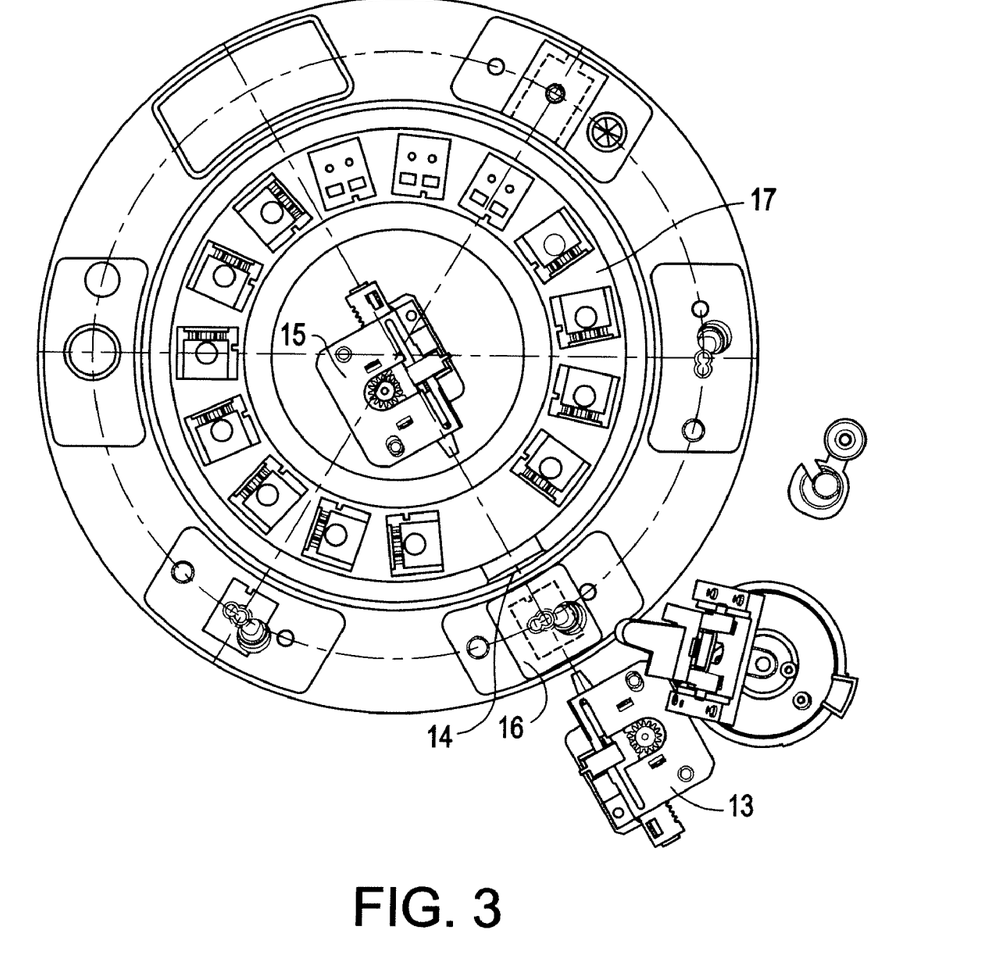
FIG. 3 shows a plan view of a desktop analyzer with the concentric rotors, centrifuge module and removable holders according to one embodiment of the present invention.

As shown in FIG. 3, the reagent rotor (1, FIG. 1) is automatically positioned to intersect the various components on the slide cartridge with the fixed location of the stationary probe system. The reagent rotor is able to move clockwise and/or counterclockwise to position the cartridges at the metering station for sample dispense and slide positioning. The reagent rotor first positions the cartridge (23) containing the test slides in front of the slide dispense mechanism (13) that will move the slide to a fixed barcode reader positioned (14) between the reagent rotor and the second, incubator rotor (17). The barcode reader reads the unique slide barcode to identify the chemistry type to be tested. A slide insert mechanism (15) reinserts the slide into the test cartridge for processing. The reagent rotor then positions the test cartridge, via the removable holder, to allow the stationary probe system (16) including tip (24) to access the disposable metering tip followed by sample aspiration from the sample reservoir (7) and then sample dispense on the top slide in the test cartridge. After sample dispensing, the top slide is transferred into the second, incubator rotor (17) by the slide dispense mechanism for incubation. The second, incubator rotor (17) is concentric to the reagent rotor and is rotated about its center axis by a motor with a sensor to determine exact positioning. A spectrometer (not shown) is located below the incubator rotor and is used to measure the slide color change specific to each assay. Immuno rate (IR) chemistries require a wash step prior to final measurement. These slides are inserted into an IR wash cartridge that contains a reusable plastic wash tip and wash fluid supply. The reagent rotor positions the IR wash cartridge at the fixed stationary probe system (16) to perform the necessary wash operation. The IR slide is reinserted into the slide incubator after washing for final measurement. Electrolyte test slides are also measured while on the slide incubator, positioned at the electrometer when measurements are to be made.

Figure 4:
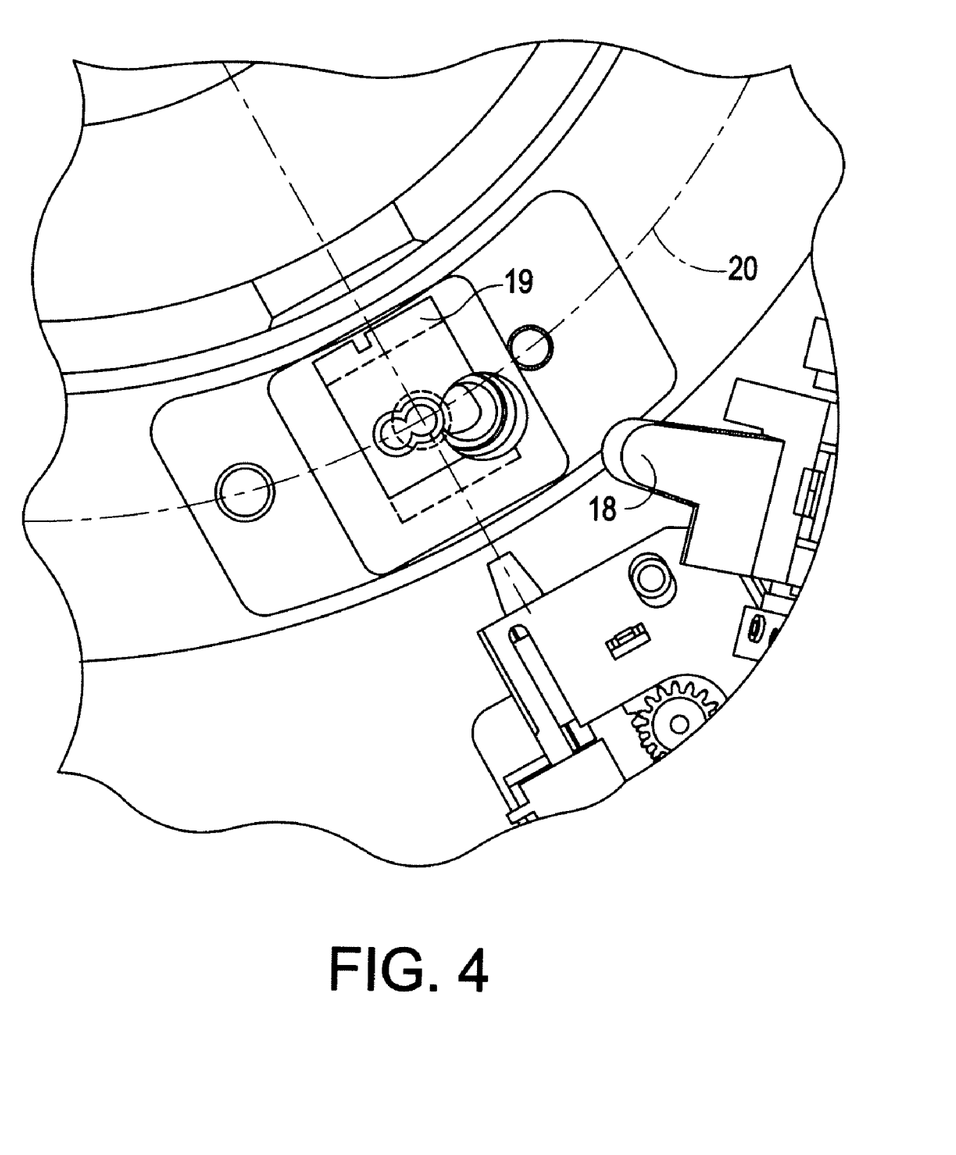
FIG. 4 shows an expanded view of the registration of the stationary fluid probe with the probe guide by the outer rotor according to one embodiment of the present invention and the same line of travel that each of the components on the removable holder share.

FIGS. 4 and 5 more closely show an embodiment that uses an additional probe. In this instance, reference metering probe system (18) is a dispensing nozzle that dispenses an electrolyte reference fluid for electrolyte chemistry or potentiometric slides (PM Slides). As shown in FIG. 4, the PM slides are processed in a similar manner as the colorimetric (CM) and immuno rate slides. Patient sample and electrolyte reference fluid are dispensed simultaneously on the PM slides (19) while in the test cartridge. In order to eliminate the need for an additional pump movement to intersect the PM slide sample spot, the slide insert mechanism will offset the PM slide slightly. That is, after barcode reading, the slide insert mechanism (15) will push the slide back into the cartridge to a point that aligns the slide underneath the probe guides (22) for metering. The center probe guide is used for sample dispense for CM and immuno rate slides. The left and right probe guides are for sample and reference fluid dispense to PM slides. This allows the CM and PM slides to intersect the common reagent rotor centerline (20), also called the "same line of travel" above. The common reagent rotor centerline (20) allows the stationary probe system (16) and hence the metering probe tip (24) to be in a fixed location while all discrete functional interactions with the reagent rotor (1) are accomplished as the reagent rotor is automatically positioned with the fixed location. As shown in FIG. 5, the additional metering system (18) may have an additional degree of freedom of movement around pivot (25) to allow access to the reservoir of reference fluid (not shown).

Figure 6:
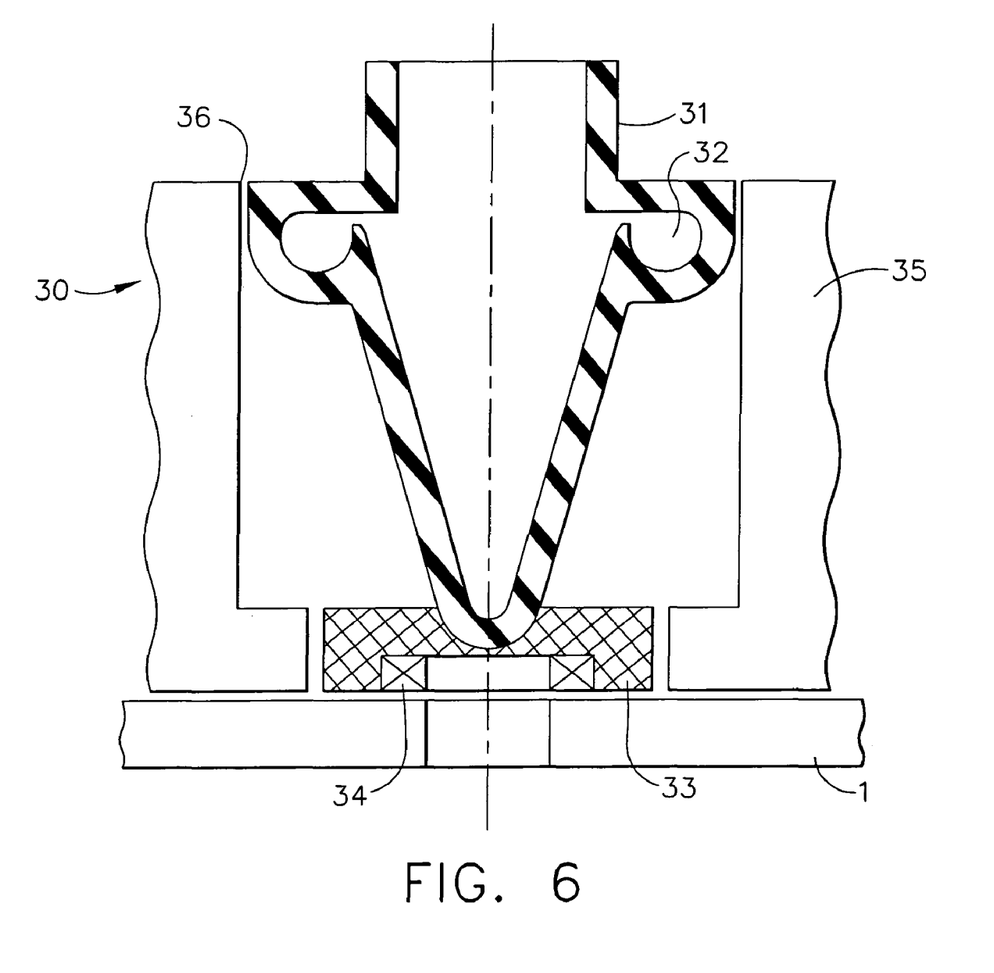
FIG. 6 shows a sectional view taken along an axis of symmetry of the centrifuge module according to one embodiment of the invention.

FIG. 6 shows a sectional view taken along the line of symmetry of the centrifuge module (30) according to a preferred embodiment. The centrifuge module includes centrifuge cup (31) that has an annular cavity (32) and a base (33). Bearings (34) support base (33) and permits rotation of the cup (31). The centrifuge module (30) includes a housing (35) that preferably has the same shape as the removable holders (2). This allows the centrifuge module (30) to be interchanged with the removable holders (2) on the outer reagent rotor (1) if desired. A gap (36) is provided between the housing (35) and cup (31) to allow rotation of the cup relative to the housing.

Figure 7:
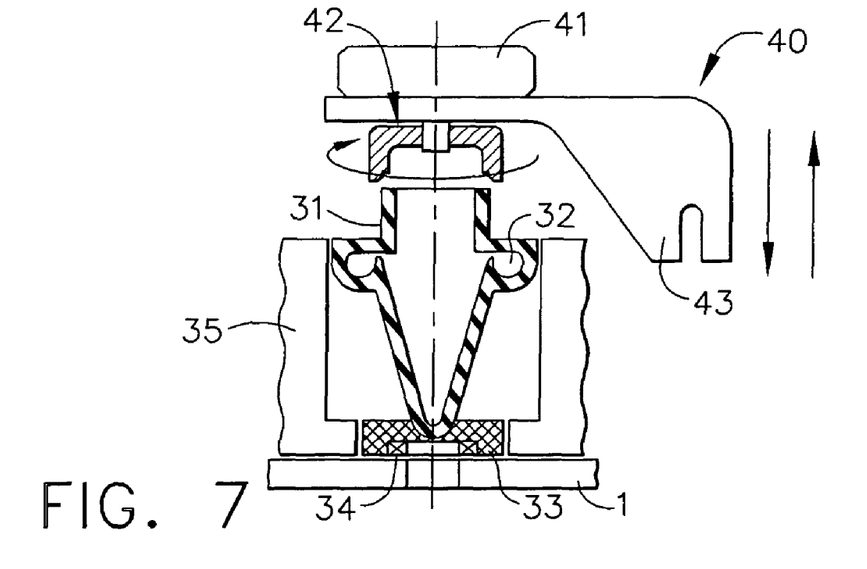
FIG. 7 shows a sectional view taken along an axis of symmetry of the centrifuge module at the centrifuge station according to one embodiment of the invention.

The centrifuge cup is rotated at a centrifuge station, schematically shown as (40) in FIG. 3 and FIG. 7. The centrifuge station includes a vertically movable bracket or spindle (43) which supports motor (41) to rotate the centrifuge cup (31). As described above, the motor can be pneumatic or electric and should be capable of rotating the cup at speeds sufficient to effect separation, preferably 30,000 to 100,000 RPM. To engage the cup with motor, an engagement mechanism (42), such as a coupling, chuck or capstan is provided on the shaft of the motor. The engagement mechanism engages the cup either by friction or in a locking engagement. In the same manner as the dispense and aspirate station, the centrifuge station can be raised and lowered to engage and disengage the centrifuge cup with the motor. Upon completion of centrifugation, the centrifugation module containing the separated sample can be transported to the dispense/aspirate station where the separated sample is aspirated into the metering tip (6).

In a preferred embodiment, the analysis sequence is implemented by a computer program interfacing with a computer, that can include a computer usable medium having computer readable program code configured to conduct the analysis.

In another preferred embodiment, the analyzer is a veterinary analyzer that includes a T4 assay.

It will be apparent to those skilled in the art that various modifications and variations can be made to the compounds, compositions and processes of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually.

We claim:
1. A desktop analyzer comprising:
a sample to be analyzed;
one or more probe tips;
one or more test elements;
a transport system;
a liquid dispense or aspirating station;
a removable holder removably located on the transport system, wherein the removable holder comprises:
 a probe tip dispenser containing the probe tips;
 a fluid supply section containing the sample to be analyzed;
 a test element recess containing the one or more test elements,
wherein the removable holder is configured to position the one or more test elements such that one or more test elements can be acted upon by the liquid dispense or aspirating station, while the one or more test elements in the recess, wherein the removable holder arranges the probe tip dispenser, fluid supply section and test element recess on the same line of travel to intersect the liquid dispense or aspirating station when the removable holder is transported to the station by the transport system;
a centrifuge module removably located on the transport system for separating a sample; and
a measurement device to analyze a sample.

2. A desktop analyzer as claimed in claim 1, wherein the transport system comprises:
a first rotor for holding the removable holder; and
second rotor arranged concentrically with the first rotor and adapted to receive a test element from the removable holder on the first rotor.

3. A desktop analyzer according to claim 2, wherein the measurement device is arranged to analyze a sample located in the second rotor; and further comprising an incubator arranged in cooperation with the second rotor to incubate a sample disposed in the second rotor.

4. A desktop analyzer as claimed in claim 2, wherein the second rotor is disposed within the first rotor.

5. A desktop analyzer as claimed in claim 1, further comprising a waste collection container located on the transport system for collecting used probe tips and test elements.

6. A desktop analyzer as claimed in claim 1, further comprising a waste collection container located on the transport system for collecting used probe tips and test elements, and wherein the waste collection container is arranged on the line of travel.

7. A desktop analyzer as claimed in claim 1, further wherein the removable holder comprises at least two removable holders.

8. A desktop analyzer as claimed in claim 7, wherein the at least two removable holders include a first removable holder and a second removable holder having different test elements.

9. A desktop analyzer as claimed in claim 8, wherein the first removable holder comprises a dry-slide test element and the second removable holder comprises an immunoassay test reaction container.

* * * * *